United States Patent
Winston et al.

(10) Patent No.: US 6,228,076 B1
(45) Date of Patent: May 8, 2001

(54) SYSTEM AND METHOD FOR CONTROLLING TISSUE ABLATION

(75) Inventors: Thomas R. Winston, Leawood; John M. Neet, Lawrence, both of KS (US)

(73) Assignee: IntraLuminal Therapeutics, Inc., Carlsbad, CA (US)

( * ) Notice: Subject to any disclaimer, the term of this patent is extended or adjusted under 35 U.S.C. 154(b) by 0 days.

(21) Appl. No.: 09/228,030

(22) Filed: Jan. 9, 1999

(51) Int. Cl.[7] .................................................. A61B 18/18
(52) U.S. Cl. ................. 606/11; 606/10; 606/12; 128/898; 356/345; 356/346
(58) Field of Search .................... 606/2, 10–12, 606/15–17; 356/345, 318, 346; 600/439; 128/664, 660.03, 303.1, 898; 250/458.1

(56) References Cited

U.S. PATENT DOCUMENTS

| | | |
|---|---|---|
| 4,675,529 * | 6/1987 | Kushida . |
| 4,718,417 * | 1/1988 | Kittrell et al. ...................... 128/303.1 |
| 5,106,387 * | 4/1992 | Kittrell et al. ........................... 606/15 |
| 5,158,560 * | 10/1992 | Sogawa et al. ......................... 606/15 |
| 5,163,432 * | 11/1992 | Ueno et al. ...................... 128/660.03 |
| 5,163,935 * | 11/1992 | Black et al. ............................ 606/17 |
| 5,601,087 * | 2/1997 | Gunderson et al. .................. 128/664 |
| 5,608,520 * | 3/1997 | Cho et al. ................................ 606/12 |
| 5,618,285 * | 4/1997 | Zair ........................................ 606/10 |
| 5,820,627 * | 10/1998 | Rosen et al. ............................ 606/15 |
| 5,920,390 * | 7/1999 | Farahi et al. .......................... 356/345 |
| 6,004,269 * | 12/1999 | Crowley et al. ...................... 600/439 |

OTHER PUBLICATIONS

Journal of Biomedical Optics, Apr. 1999, pp. 236–237, Barry R. Masters, Early Development of Optical Low–Coherence Reflectometry and Some Recent Biomedical Applications, Department of Ophthalmology, University of Bern, Bern, Switzerland.

\* cited by examiner

*Primary Examiner*—Lee Cohen
*Assistant Examiner*—Ahmed Farah
(74) *Attorney, Agent, or Firm*—Armstrong Teasdale LLP

(57) ABSTRACT

A control system and method for controlling tissue ablation uses optical time domain reflectometry data to differentiate abnormal tissue from normal tissue, and to control ablation of abnormal tissue by controlling a tissue ablative apparatus. Using data provided by an interferometric apparatus, the control system provides control signals to the tissue ablative apparatus, controlling activation of the tissue ablation apparatus so that normal tissue is left untreated while abnormal tissue is ablated.

34 Claims, 3 Drawing Sheets

SYSTEM AND METHOD FOR CONTROLLING TISSUE ABLATION

BACKGROUND OF THE INVENTION

This invention relates generally to systems and methods for controlling medical devices, and more particularly, to a control system and methods for controlling tissue ablation.

Many medical treatments involve the removal of diseased or damaged tissue from within the body. For example, common surgical practice requires the excision of tumors, cysts, and polyps, which may appear in any area of the body, and the removal of atherosclerotic plaque from arteries. Classical surgical techniques require a properly trained surgeon to directly view the tissue being treated to determine which, and how much, of the tissue can safely be removed. This type of procedure is highly invasive and typically requires a lengthy recovery period for the patient.

More modern, less invasive surgical tissue removal techniques are known. Generally these techniques greatly benefit the patient, but present new challenges for the surgeon. For example, catheters, endoscopes and laparoscopes are now commonly used for a variety of surgical procedures and require minimal entry into the body. Use of these techniques generally decreases surgical trauma and recovery time, and improves outcome, but also incur significant disadvantages for the surgeon. Particularly, such techniques impair visualization of the affected region and substantially limit surgical working space. For example, optical fiber endoscopes are known but cannot be used in a blood field without first clearing the blood with a saline solution. Ultrasound probes are known but often produce false echoes when used for looking forward through, for example, the lumen of an artery. Fluoroscopy is known but is two-dimensional and exposes the patient and medical personnel to various forms of radiation.

Impaired visualization of the surgical field makes removal of diseased tissue difficult. In particular, the use of high energy tissue ablation devices such as those powered by lasers, radio frequency transmission, microwaves and the like, is risky under conditions of impaired visualization because poor discrimination of healthy tissue from diseased tissue can result in damage of healthy tissue. Accordingly, a surgeon operating such an ablation device must advance it extremely cautiously, perhaps missing diseased tissue which should be removed.

It would therefore be desirable to provide a precise and reliable method for controlling the activation and advancement of tissue ablative devices. It would also be desirable to provide an improved method for visualizing internal body tissues being treated with minimally invasive tissue ablative devices. It would also be desirable to provide an improved method and apparatus for differentiation of abnormal tissue from normal tissue.

BRIEF SUMMARY OF THE INVENTION

In an exemplary embodiment, a method for controlling tissue ablation uses optical time domain reflectometry data to differentiate abnormal tissue from normal tissue, to control ablation of abnormal tissue by controlling the delivery of energy to a tissue ablation element. Using data provided by an interferometric apparatus, a control system provides control signals to tissue ablative apparatus and controls activation of the tissue ablation apparatus so that normal tissue is left untreated while abnormal tissue is ablated.

In one aspect, the present invention is directed to using interference data to identify an interface between abnormal tissue and healthy or normal tissue, and altering the delivery of energy to the tissue ablative apparatus in response to identification of an interface. In one embodiment, the control system includes a microprocessor and an energy controller. The control system is coupled to an interferometric apparatus for providing interfering light beams which produce the interferometric data. More specifically, for example, a low coherence light source producing a light beam is coupled to a beam splitter which splits the beam into two beams, a first or reference beam, and a second or sampling beam, which are transmitted respectively down a first optical fiber, and a second optical fiber. The second optical fiber extends through the lumen of a support member such as a catheter so that a distal, sampling end of the second optical fiber can be positioned near a sample, such as an internal body tissue to be inspected. The first optical fiber is positioned outside the body. The first beam is reflected at the distal or free end of the first optical fiber by a reflector coupled thereto, while the second beam is reflected at the distal sampling end by the sample. The lengths of the first and second optical fibers are adjustable with, for example, a piezoelectric coil. The reflected beams interfere with one another when recombined at the beam splitter. The path length difference between the recombined beams produces a pattern of interference which is detected by a detecting element coupled to the beam splitter. The detecting element provides the interference data to the control system, in which the microprocessor generates a psuedoimage of the sample, and detects interfaces between normal and abnormal tissue. In response to the detection of such an interface, the microprocessor generates and supplies control signals to the energy controller, which accordingly alters the delivery of energy to the tissue ablative apparatus.

In another aspect, the present invention is directed to providing a psuedoimage of a tissue sample for visual display to an individual who is manually advancing a tissue ablative element of the tissue ablative apparatus. In an exemplary embodiment, the microprocessor is coupled to an output display device such as a monitor. The psuedoimage data generated by the microprocessor is displayed on the monitor so that the operator has a visual image while manually advancing the tissue ablative element. The operator can advance while watching the image until, for example, the control system detects an interface and alters the delivery of energy to the tissue ablative apparatus.

The control system and method provide for minimally invasive control of tissue ablation. Further, the system provides high resolution image data so that tissue ablation can be controlled at a very fine scale. In addition, the system and method provide for improved differentiation of abnormal tissue from normal tissue.

DETAILED DESCRIPTION OF THE INVENTION

Figure 1:
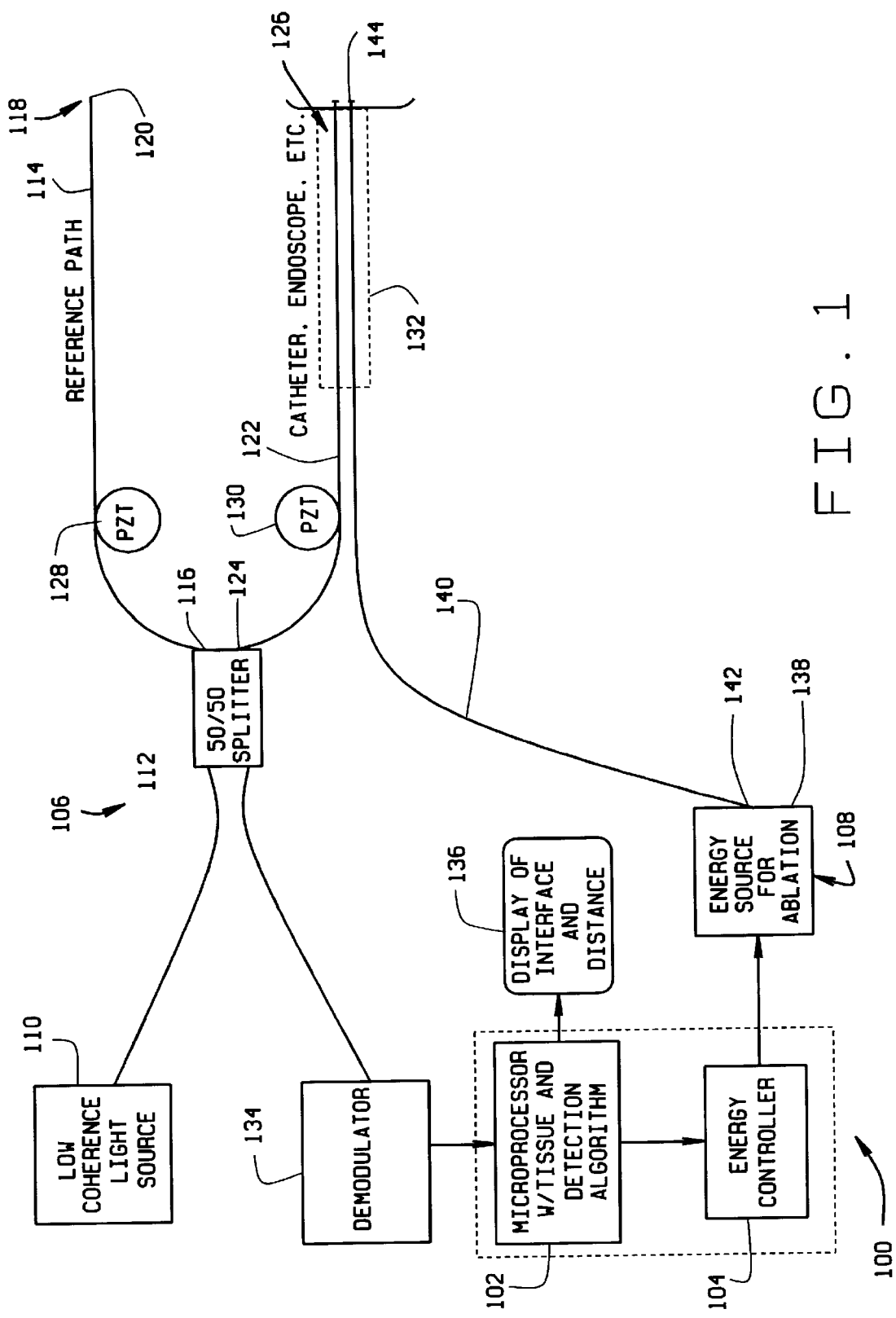
FIG. 1 is a schematic illustration of a control system for controlling tissue ablation.

FIG. 1 is a schematic illustration of an exemplary embodiment of a control system 100. Generally, control system 100 includes a microprocessor 102 coupled to an energy controller 104, and is shown in FIG. 1 coupled to interoferometric apparatus 106 and tissue ablative apparatus 108. Microprocessor 102, utilizing an output supplied by interferometric apparatus 106, generates an output signal which is supplied to energy controller 104. Using the output signal supplied by microprocessor 102, energy controller 104 alters, or adjusts, an energy signal supplied to tissue ablative apparatus 108. Additionally, the output of microprocessor 102 can be used to generate a pseudoimage on an output device as described below.

A control algorithm as described below may be implemented in microprocessor 102 and practiced using data collected by interoferometric apparatus 106. It will be apparent to those skilled in the art that, of course, such an algorithm may be practiced with many alternative microprocessors, and is not limited to practice only in connection with those integrated circuits referred to in the art as microprocessors. Therefore, and as used herein, the term microprocessor refers to microcomputers, processors, microcontrollers, application-specific integrated circuits, and other programmable circuits. In addition, the present application is directed to the control methods and system as described below in more detail. It should be understood that such methods and systems should not be limited to a particular interferometric apparatus or tissue ablative apparatus as described below in an exemplary embodiment.

Interferometric apparatus 106 typically includes a light source 110 coupled to a beam splitter 112. In one embodiment, light source 110 is a low coherence light source having a power of about 100 microWatts to about 25 milliWatts. While the light source may be varied, sources that emit short coherent wavelengths of about 0.7 to about 2.0 microns are more desirable than those emitting longer wavelengths because shorter wavelengths allow better imaging properties and penetration. However, the light source may be varied to adjust the wavelength of the light to between about 0.3 to about 5.0 microns, to optimize the imaging resolution of the tissue expected to be encountered. For example, light of a wavelength of about 1.3 microns has been found to be optimal for penetrating through atherosclerotic plaque and imaging the adventitia and media inside of a diseased artery. A first, reference optical fiber 114 is coupled at a proximal end 116 to beam splitter 112, and has a free or distal end 118 with a reflector 120, such as a mirrored surface, coupled thereto. A second, sampling optical fiber 122 is coupled at a proximal end 124 to beam splitter 112, and has a distal sampling end 126 for placement near or adjacent an internal body tissue T. To adjust the relative lengths of first optical fiber 114 and second optical fiber 122, first optical fiber 114 is wrapped around a first piezoelectric coil 128, and second optical fiber 122 is wrapped around a second piezoelectric coil 130. Other devices or elements for adjusting the relative lengths of the optical fibers are known in the art. Second optical fiber 122 extends through a lumen of a support member 132 such as, for example, a catheter or an endoscope. Beam splitter 112 has an output coupled to a detecting element 134 which includes, for example, a photodetector, a demodulator and an analog digitizer (not shown). Detecting element 134 has an output coupled to microprocessor 102. Microprocessor 102 can be further coupled to an output display device 136 such as a computer monitor for visual display of data.

First optical fiber 114 and second optical fiber 122 are, for example, a type commonly used in medical imaging, having a total outside diameter of less than about 150 microns. In one embodiment, suitable optical fibers are fabricated from drawn or extruded glass or plastic having a central core and a cladding of a lower refractive index material to promote internal reflection. The diameter of the optical fibers may be varied to optimize transmission of the particular wavelength of light chosen, and to obtain clearance through the lumen of support member 132. For example, for light having a wavelength of 1300 nm, a single mode optical fiber having a diameter of 125 microns with a total outside diameter of about 150 microns would be suitable. Optical fibers having smaller diameters of about 80 microns are also available and can be used when greater clearance through the lumen of support member 132 is desired, or alternatively, bundles of optical fibers may be used.

Tissue ablative apparatus 108, in one embodiment, includes an energy source 138 such as a laser energy source, for tissue ablation. Energy source 138 is coupled to a tissue ablative device 140 at a proximal end 142 of tissue ablative element 140. Tissue ablative element 140 can be, for example, a laser catheter. In any case, tissue ablative element 140 has a distal end 144 and extends through support member 132 so that distal end 144 can be positioned near tissue T.

In an exemplary embodiment, energy source 138 for tissue ablative element 140 is a laser source, and tissue ablative element 140 is a laser catheter including at least one optical fiber (not shown) extending through support member 132 for transmitting a laser beam from the laser source to tissue T, so that tissue inspection and ablation can be accomplished simultaneously. In an alternative embodiment in which energy source 138 is again a laser source, ablative element 140 shares first optic fiber 114 with interoferometric apparatus 106, and input to first optic fiber 114 is switched with a second beam splitter (not shown) between interoferometric apparatus 106 and the laser source so that inspection of tissue T and ablation occur alternately. Alternatively, tissue ablative element 140 may be, for example, a radio frequency device, mechanical cutting or atherectomy device, ultrasound device, microwave device or other minimally invasive tissue ablation device. Energy source 138 can accordingly be a radiofrequency source, source for mechanical energy, ultrasound source, microwave source, or the like.

Figure 2:
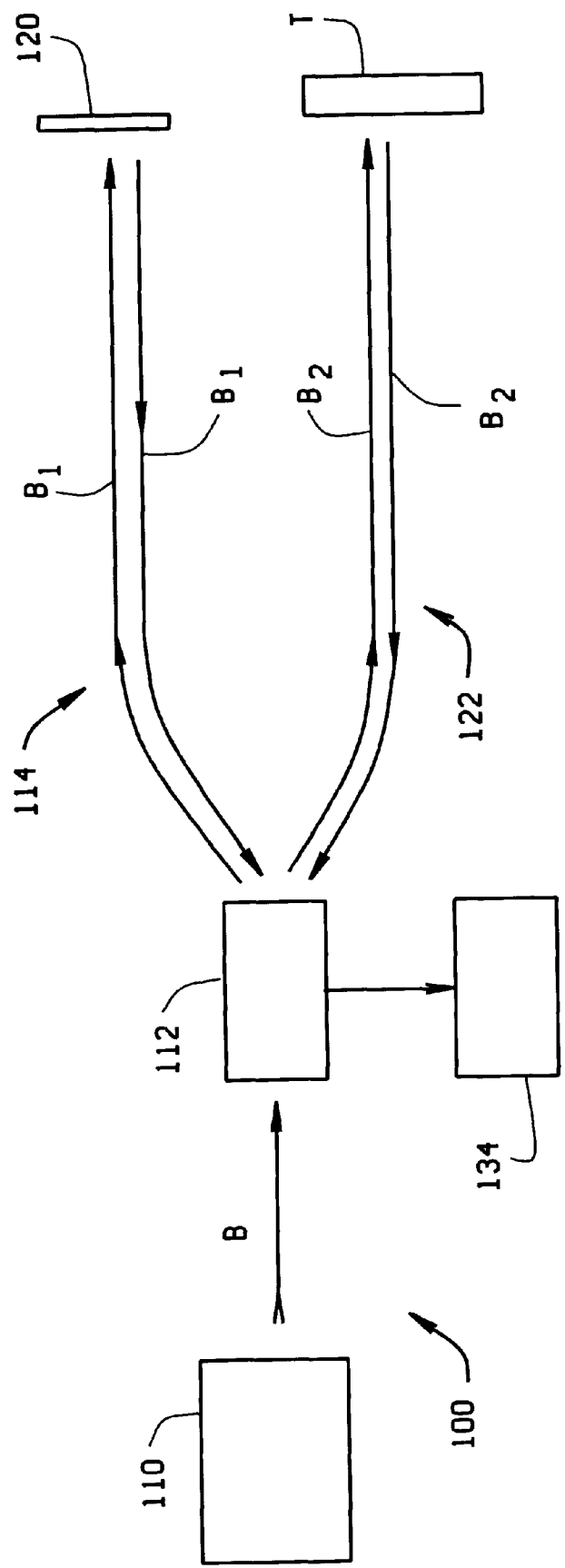
FIG. 2 is a schematic illustration of the principles of optical coherence domain reflectometry on which the control system for controlling tissue ablation is based.

FIG. 2 is a schematic illustration of the principles of optical coherence domain reflectometry on which control system 100 is based. In use, for example, support member 132 is positioned internally in a body, for example by inserting into a body passage or surgical incision, so that second optic fiber distal end 126 is positioned within the body near tissue T to be inspected. First optic fiber 114 is positioned external to the body. Light source 110 is energized to produce a light beam B which is transmitted to beam splitter 112. Beam splitter 112 is configured to split beam B from light source 110 into a reference beam $B_1$ and a sampling beam $B_2$. Beam splitter 112 directs reference beam $B_1$ along first optical fiber 114 toward reflector 120, and second beam $B_2$ along second optical fiber 122 toward tissue T. $B_1$ is reflected back along first optical fiber 114 by reflector 120, and $B_2$ is reflected back along second optical fiber 122 by tissue T.

$B_1$ and $B_2$ are recombined at beam splitter 112 and interfere constructively with each other when their respective path lengths are equivalent with one another. The distance over which interference occurs can be determined by the coherence function of the light source. Typically the coherence length is about 15 microns for a low coherence light source having a power of about 100 microWatts to about 25 milliWatts.

The optical path length of light beam $B_2$ depends on the length of second optical fiber 122. The optical path length of light beam $B_1$ depends on the length of first optical fiber 114 and the distance in the tissue from where the light is scattered (reflected), adjusted for the change in the group refractive index difference of the tissue. Referring again to FIG. 1, the optical distances along optical fibers 114 and. 122 can be varied by actuating piezoelectric coils 128 and 130. By continually varying the optical path lengths, the tissue depth can be scanned such that the intensity of light scattering from a series of specific depths can be measured. For example, when the optical path length of $B_1$ is 0.5 mm longer than the optical path length of $B_2$, the intensity of light scattered from an optically equivalent (adjusted for the change in group refractive indices) depth of 0.5 mm in the tissue is measured. The optical path lengths are continually varied, and intensity of scattered light measured to develop a function of scattering intensity versus distance. Thus, the interferometric technique precisely measures very small distances and thicknesses, so that a high resolution image of tissue T can be formed, providing on-line, high resolution information to determine if ablative device 140 can be safely enabled or advanced. Further details on the interferometric technique and interferometric apparatus are described in co-pending U.S. patent application Ser. No. 09/060,487 (filed Apr. 15, 1998), which is assigned to the present assignee, and which is incorporated herein, in its entirety, by reference. In alternate embodiments, in place of interferometric apparatus 106, control system 100 is instead coupled to an apparatus which uses a different technique for analyzing reflected light, such as Raman or Rayleigh spectroscopy, induced fluorescence, or other linear or non-linear techniques. For example, when coupled to a spectroscopic apparatus, microprocessor 102 uses analysis of spectroscopic data to identify an interface between abnormal and normal tissue.

Figure 3:
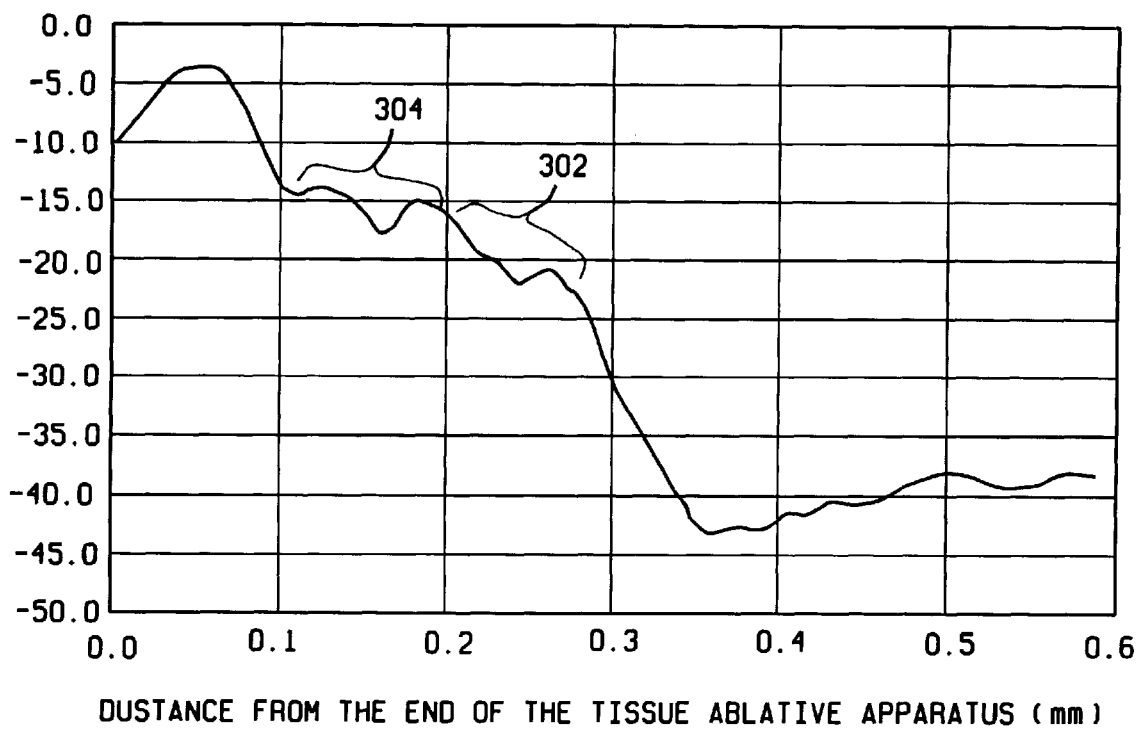
FIG. 3 is a graph showing the scattering effects on a light beam of a diseased artery having a layer of atheroscleotic plaque.

FIG. 3 is a graph showing the scattering effects on light beam $B_2$ of an abnormal tissue: an area of plaque 302 in a diseased artery. The graph shows intensity of reflected light in decibels as a function of distance from distal end 126 of second optical fiber 122. On such a graph, plaque area 302 is distinguishable from an area 304 of normal, healthy artery tissue by an increased and steady decay of reflected light intensity as a function of distance. More specifically, by determining the slope of the decay, abnormal tissue is identified as described below in more detail. The steady decay exhibited in area 302 relative to area 304 is attributable to the relatively unorganized structure of abnormal tissue, in this case plaque, which tends to scatter light in random directions, thereby decreasing the intensity of reflected light transmitted back through second optical fiber 122. The relatively more organized structure of normal tissue, in this case healthy arterial wall, scatters the light in a birefringent or anisotropic pattern so that relatively more light is reflected back through second optical fiber 122.

Microprocessor 102 supplies control signals to energy controller 104. More specifically, the control algorithm detects the presence of abnormal tissue by examining the rate of decay of reflected light intensity as a function of distance from distal end 126 of second optical fiber 122. For example, microprocessor 102 samples the reflected light at about 10 hertz, and generates a sliding average of multiple points, for example averaging the intensity value over a window of about 8 to about 30 points at a time. The sliding average identifies inflection points in the function which represent a true or actual change in the slope of the function, as opposed to noise. An actual change in slope identifies an interface between normal tissue and abnormal tissue. For example, using a light source of about 100 microWatts, emitting light at a wavelength of 1300 nm, normal tissue is identified by regions of the function having a slope of less than about −75 dB/mm. Regions of the function having a slope within the range of about −75 dB/mm to about −150 dB/mm indicate a soft plaque such as a fatty or lipid plaque. A slope within about −150 dB/mm to about −200 dB/mm would indicate a calcified plaque, while a slope greater than about −200 dB/mm indicates air or blood. The algorithm is, for example, a simple go/no-go algorithm in which the inflection points between regions of the function having different slopes are used to determine the state of control signals supplied to energy controller 104 to either enable or disenable tissue ablative device 140. In alternative embodiments, the algorithm can be configured to perform a more complex pattern recognition or noise analysis which identifies the changes in reflected light which characterize the interfaces between normal and abnormal tissue.

For example, FIG. 3 shows reflected light intensity as a function of distance in an artery, using a light source of about 100 microWatts emitting light at a wavelength of 1300 nm. From about 0.100 mm to about 0.200 mm from distal end 126 of second optical fiber 122, the slope of the function is less than about −75 dB/mm, which indicates normal, healthy tissue in area 304. At approximately 0.200 mm from distal end 126, the slope of the function changes, which microprocessor 102 identifies as an interface between normal tissue (arterial wall) and abnormal tissue, in this case a plaque. The slope of the function from about 0.200 mm to about 0.275 mm, plaque area 302, from distal end 126 is about −100 dB/mm. This slope falls within the range of about −75 dB/mm to about −150 dB/mm, which indicates a soft plaque such as a fatty or lipid plaque. At about 0.275 mm from distal end 126, the slope of the function again changes, and microprocessor 102 identifies an interface. In this case, the slope of the function from about 0.275 mm to about 0.350 mm from distal end 126 is about −267 dB/mm, indicating air or blood, so that microprocessor 102 identifies an interface between the end of a plaque and air or blood at 0.275 mm from distal end 126. A change in slope representing a decrease in decay of reflected light as a function of distance (i.e. a decrease in slope), not shown, would identify an interface between the end of a plaque and normal tissue.

Figure 4:
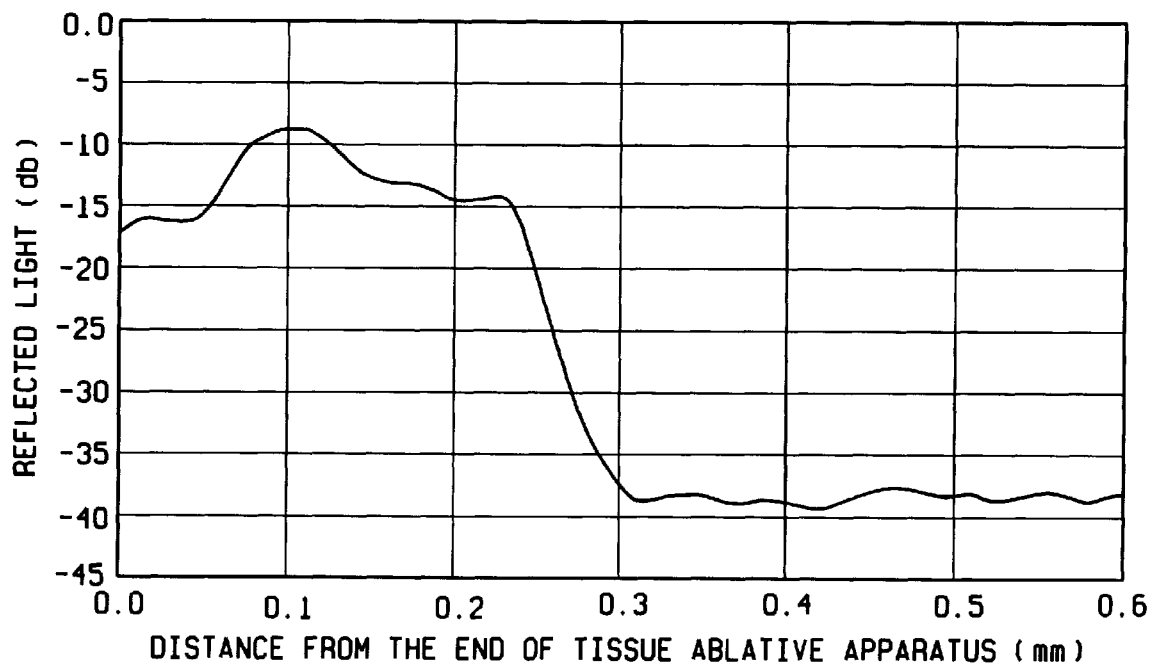
FIG. 4 is a graph showing the scattering effects on a light beam of a healthy artery.

FIG. 4 shows the intensity of reflected light as a function of distance in a normal, healthy artery, using a light source of about 100 microWatts emitting light at a wavelength of 1300 nm. The function from about 0.100 mm to about 0.230 mm from distal end 126 has a slope of about −70 dB/mm, indicating normal tissue. At about 0.230 mm, the slope of the function from about 0.230 mm to about 0.290 mm increases to about −400 db/mm, indicating blood in the artery.

In typical use, for example, distal end 144 of disenabled tissue ablative element 140 is positioned within a normal section of artery and advanced along a longitudinal axis of the artery defined by the length of second optical fiber 122. The start of an area or region of abnormal tissue, such as an atherosclerotic plaque, is identified when microprocessor 102 identifies a normal tissue/abnormal tissue interface ahead of second optic fiber distal end 126 (and distal end 144 of tissue ablative element 140). Tissue ablative element distal end 144 is advanced just past the interface, e.g., the start of the plaque, and then microprocessor 102 supplies signals to energy controller 104 to activate energy source 138 so that tissue ablative device 140 is enabled and the abnormal tissue (plaque) is ablated. In one embodiment, to insure that normal tissue is not inadvertently damaged, a small area or region of plaque behind the area where ablative element 140 is first enabled can be left remaining. Tissue ablative element 140 is advanced through the plaque, and can be safely enabled as long as no tissue interface between the abnormal tissue (plaque) and normal tissue is detected by microprocessor 102. In one embodiment, when microprocessor 102, using the output of interferometric apparatus 106, identifies an interface between the abnormal (plaque) tissue and normal tissue ahead of second optic fiber distal end 126, microprocessor 102 accordingly supplies signals to energy controller 104 to deactivate energy source 138 so that tissue ablative element 140 is disenabled before reaching the normal tissue, and normal tissue is undamaged by tissue ablative element 140. A small area or region of plaque at the end of the plaque relative to tissue ablative element distal end 144 may be left remaining, to insure that normal tissue is undamaged by tissue ablative element 140. However, it should be recognized by those skilled in the art that the relative position of tissue ablative element 140 with respect to an abnormal/normal or normal/abnormal tissue interface, at which tissue ablative element 140 is enabled or disenabled, can be varied. Further, the amount of energy delivered to tissue ablative element 140 can be adjusted depending on whether a soft plaque or calcified plaque has been identified. For example, if a calcified plaque is identified, a lower amount of energy can first be delivered to tissue ablative element 140. If the plaque is not ablated using a lower amount of energy, then the energy can be upwardly adjusted to ablate the calcified plaque.

In an exemplary embodiment, control system 100 performs real-time control of tissue ablation without further input from an operator. In an alternative embodiment, control system 100 is further linked to a stepping motor or the like, which is linked to tissue ablative element 140 and to microprocessor 102. The stepping motor responds to control signals from microprocessor 102 by advancing or retracting tissue ablative element 140 so that both enablement and advancement of tissue ablative element 140 are automatically controlled by control system 100. For example, after abnormal tissue has been detected and tissue ablative element 140 enabled, tissue ablative element 140 is advanced as long as a tissue interface between the abnormal tissue and normal tissue is not detected. Tissue ablative element 140 continues to advance until such a tissue interface is identified, indicating normal tissue ahead of tissue ablative element 140. Once such an interface is identified, tissue ablative element 140 is disenabled and can be retracted. In an alternative method of use, a manual operator of tissue ablative element 140 may view the pseudoimage on output display device 136 for real-time imaging of the tissue so that the operator can accordingly respond by manually activating or deactivating the energy controller, or by manually advancing or retracting ablative element 140. Because second optical fiber 122 can be used simultaneously and side-by-side with tissue ablative element 140, the system can provide continuous, high resolution imaging data to the operator as tissue ablative element 140 is advanced.

The control system thus provides high resolution imaging data for automated or manual control of minimally invasive tissue ablative devices. In an alternative embodiment, a variety of tissue ablative modalities, devices and probes, including radio frequency devices, microwave devices, ultrasound devices, mechanical cutting or atherectomy devices and laser catheters, as known in the art, are used with control system 100. Further, the guidance system can be used simultaneously with the tissue ablative element to provide continuous online information regarding the tissue being treated, as the tissue ablative element is being advanced.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for controlling tissue ablation using a tissue ablation system, the tissue ablation system including a control system coupled to tissue ablative apparatus and to interferometric apparatus, the control system configured to use interferomtric data from the interferomtric apparatus to detect interfaces between normal and abnormal tissue, said method comprising the steps of:

generating interferometric data from a tissue with the interferometeric apparatus;

providing the interferometric data to the control system to detect whether an interface between an abnormal tissue and a normal tissue is present; and if an interface is present, generating control signals with the control system to alter the operation of the tissue ablative apparatus.

2. A method in accordance with claim 1 wherein detecting whether an interface between an abnormal tissue and a normal tissue is present comprises the step of detecting whether abnormal tissue is present.

3. A method in accordance with claim 2 wherein altering the operation of the tissue ablative apparatus comprises the step of enabling the tissue ablative apparatus so that the abnormal tissue is ablated.

4. A method in accordance with claim 3 wherein detecting whether an interface between an abnormal tissue and a normal tissue is present further comprises the step of advancing the tissue ablative apparatus into an area having abnormal tissue until normal tissue is detected.

5. A method in accordance with claim 4 wherein altering the operation of the tissue ablative apparatus further comprises the step of, if normal tissue is detected, then disenabling the tissue ablative apparatus.

6. A method in accordance with claim 1 wherein detecting whether an interface between an abnormal tissue and a normal tissue is present comprises the step of detecting whether normal tissue is present.

7. A method in accordance with claim 6 wherein detecting whether an interface between an abnormal tissue and a normal tissue is present further comprises the step of, if normal tissue is present, altering the position of the tissue ablative apparatus until abnormal tissue is detected.

8. A method in accordance with claim 7 wherein the tissue ablative apparatus includes a stepping motor, and wherein altering the position of the tissue ablative apparatus comprises the step of altering control signals supplied to the stepping motor.

9. A method in accordance with claim 7 wherein altering the operation of the tissue ablative apparatus comprises the steps of:

if abnormal tissue is detected, then advancing the tissue ablative apparatus into the abnormal tissue; and enabling the tissue ablative apparatus.

10. A method in accordance with claim 1 wherein the control system is coupled to an interferometric apparatus, and wherein detecting whether an interface is present comprises the steps of:

generating interference data; and using the interference data to identify the interface between an abnormal tissue and a normal tissue.

11. A method in accordance with claim 10 wherein the interferometric apparatus includes a sampling optical fiber having a distal sampling end, and wherein detecting whether an interface between normal tissue and abnormal tissue is present comprises the steps of:

generating a function from the interference data for reflected light intensity versus distance from the sampling end of the sampling optical fiber; and examining the rate of decay of the function.

12. A method in accordance with claim 11 wherein examining the rate of decay of the function comprises the step of identifying actual inflection points of the function.

13. A method in accordance with claim 10 further comprising the step of using the interference data to generate a psuedoimage of a tissue.

14. A method in accordance with claim 1 wherein the control system is coupled to a spectroscopic apparatus, and wherein detecting whether an interface is present comprises the steps of:

generating spectroscopic data; and using the spectroscopic data to identify an interface between abnormal tissue and normal tissue.

15. A method in accordance with claim 1 wherein the tissue ablative apparatus includes a tissue ablative element coupled to an energy source, the energy source coupled to the control system, and wherein altering the operation of the tissue ablative apparatus comprises the step of altering control signals supplied to the energy source.

16. A control system for controlling tissue ablative apparatus, said control system comprising:

a microprocessor and an energy controller, said control system configured for coupling to the tissue ablative apparatus and to interferometric apparatus, said control system configured to use interferometric data from the interferometric apparatus to detect whether an interface between an abnormal tissue and a normal tissue is present and if an interface is present, to generate control signals to the energy controller to alter the operation of the tissue ablative apparatus.

17. A system in accordance with claim 16 wherein the interferometric apparatus includes a sampling optical fiber having a distal sampling end, and wherein to detect whether an interface between normal tissue and abnormal tissue is present, said system is configured to:

generate a function for reflected light intensity against distance from the sampling end of the sampling optical fiber utilizing the interference data; and determine a rate of decay of the function.

18. A system in accordance with claim 17 wherein to determine the rate of decay of the function, said system is configured to identify actual inflection points of the function.

19. A system in accordance with claim 16 further configured to generate a psuedoimage of a tissue utilizing the interference data.

20. A system in accordance with claim 16 wherein a spectroscopic apparatus configured to generate spectroscopic data is coupled to said control system, and wherein to detect whether an interface is present, said system is configured to:

identify an interface between abnormal tissue and normal tissue using the spectroscopic data.

21. A system in accordance with claim 20 wherein the spectroscopic apparatus comprises Raman spectroscopic apparatus.

22. A system in accordance with claim 20 wherein the spectroscopic apparatus comprises Rayleigh spectroscopic apparatus.

23. A system in accordance with claim 16 wherein to alter the operation of the tissue ablative apparatus, said system is configured to enable the tissue ablative apparatus to ablate the abnormal tissue, if an interface between normal and abnormal tissue is detected.

24. A system in accordance with claim 16 wherein to alter the operation of the tissue ablative apparatus, said system is configured to disenable the tissue ablative apparatus so that the normal tissue is unharmed, if an interface between abnormal and normal tissue is detected.

25. A system in accordance with claim 16 wherein the tissue ablative apparatus includes a tissue ablative element coupled to an energy source, the energy source coupled to said control system, and wherein to alter the operation of the tissue ablative apparatus, said system is configured to alter control signals supplied to the energy source.

26. A system in accordance with claim 16 wherein the tissue ablative apparatus includes a stepping motor, and wherein to alter the operation of the tissue ablative apparatus, said system configured to alter control signals supplied to the stepping motor.

27. A tissue ablation system for ablating tissue, said system comprising:

tissue ablative apparatus comprising a tissue ablative element and an ablation energy source;

interferometric apparatus comprising a low coherent light source, for providing interference data; and a control system coupled to said interferometric apparatus, said control system comprising a microprocessor and an energy controller coupled to said ablation energy source for altering an energy signal supplied to said tissue ablative apparatus, said control system configured to use the interference data to detect whether an interface between normal tissue and abnormal tissue is present and if the interface is present, alter the energy signal supplied to the tissue ablative apparatus.

28. A system in accordance with claim 27 wherein said tissue ablative element comprises a laser catheter.

29. A system in accordance with claim 27 wherein said tissue ablative element comprises a radio frequency device.

30. A system in accordance with claim 27 wherein said tissue ablative element comprises a mechanical atherectomy device.

31. A system in accordance with claim 27 wherein said tissue ablative element comprises an ultrasound device.

32. A system in accordance with claim 27 wherein said tissue ablative element comprises a microwave device.

33. A system in accordance with claim 27 further comprising an output display device coupled to said microprocessor.

34. A system in accordance with claim 33 wherein said output display device comprises a computer monitor.

* * * * *